(12) United States Patent
Park et al.

(10) Patent No.: US 8,926,334 B2
(45) Date of Patent: Jan. 6, 2015

(54) INJECTION SIMULATION SYSTEM AND METHOD

(75) Inventors: Se Hyung Park, Seoul (KR); Lae Hyun Kim, Seoul (KR); Seung Jae Shin, Seoul (KR); Deuk Hee Lee, Seoul (KR); Wan Joo Park, Goyang-si (KR); Hyun Chul Cho, Ulsan (KR); Hyun Jeong Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 25 days.

(21) Appl. No.: 13/576,428

(22) PCT Filed: Jan. 27, 2011

(86) PCT No.: PCT/KR2011/000590
§ 371 (c)(1),
(2), (4) Date: Aug. 1, 2012

(87) PCT Pub. No.: WO2011/096673
PCT Pub. Date: Aug. 11, 2011

(65) Prior Publication Data
US 2012/0301858 A1 Nov. 29, 2012

(30) Foreign Application Priority Data
Feb. 2, 2010 (KR) .......................... 10-2010-0009437
Jan. 25, 2011 (KR) .......................... 10-2011-0007464

(51) Int. Cl.
*G09B 23/28* (2006.01)
*A61M 5/46* (2006.01)

(52) U.S. Cl.
CPC ............... *A61M 5/46* (2013.01); *G09B 23/285* (2013.01)
USPC .......................................... 434/272; 434/262

(58) Field of Classification Search
USPC .................................... 434/262–275; 604/143
See application file for complete search history.

(56) References Cited

U.S. PATENT DOCUMENTS

2005/0277096 A1    12/2005   Hendrickson et al.
2006/0194180 A1*   8/2006    Bevirt et al. .................. 434/262

FOREIGN PATENT DOCUMENTS

| JP | 02-053067   | 4/1990 |
| JP | 05-027675   | 2/1993 |
| JP | 10-260627   | 9/1998 |
| JP | 2000-010467 | 1/2000 |

* cited by examiner

*Primary Examiner* — Timothy A Musselman
(74) *Attorney, Agent, or Firm* — NSIP Law

(57) ABSTRACT

Provided is an injection simulation system and method. The system includes a syringe comprising an injection needle, a haptic unit which measures an insertion angle and insertion depth of the injection needle, and which comprises a motor unit that is driven by a haptic force corresponding to the measured insertion angle and insertion depth. The system also includes a control unit which calculates the haptic force corresponding to the insertion angle and the insertion depth, and transmits the calculated haptic force to the motor unit of the haptic unit.

13 Claims, 8 Drawing Sheets

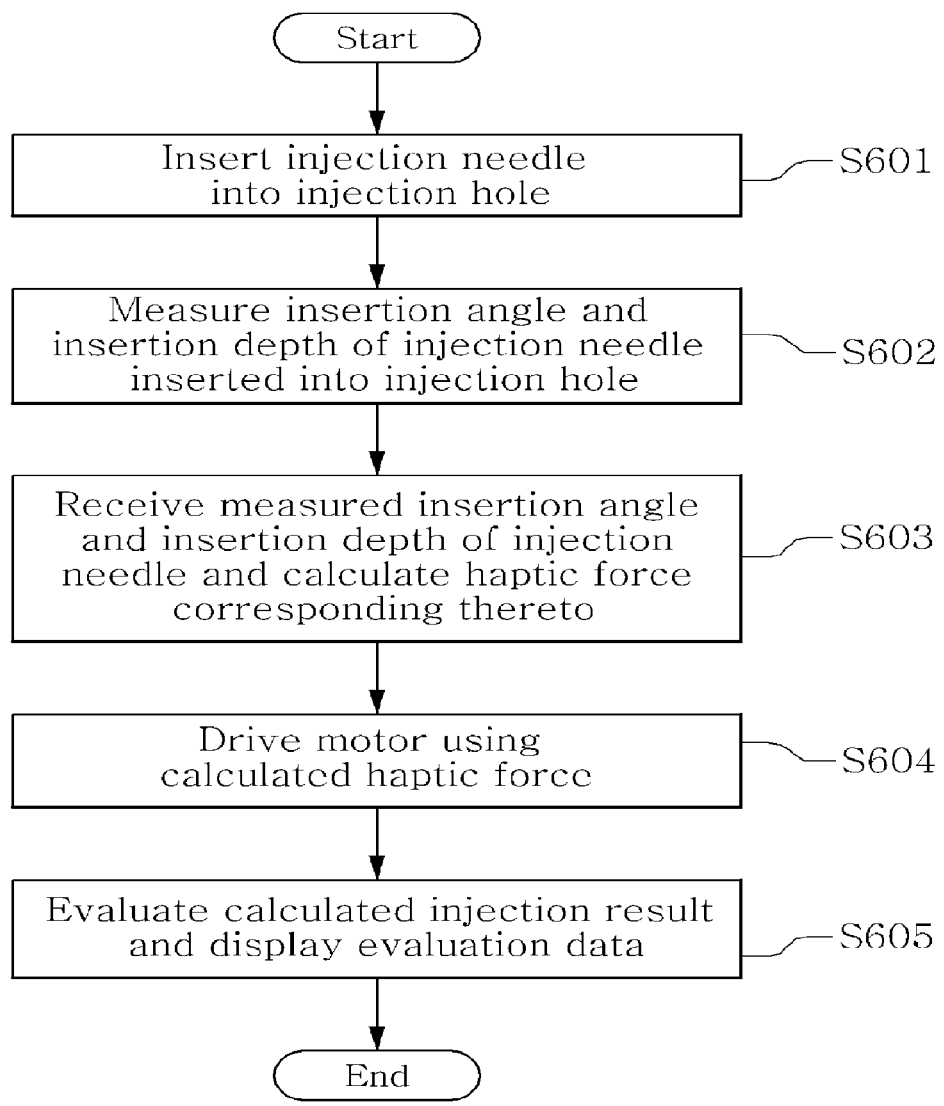

INJECTION SIMULATION SYSTEM AND METHOD

This application is a national stage application of International Application No. PCT/KR2011/000590, filed on Jan. 27, 2011, which claims the benefit of Korean Patent Application No. 10-2010-0009437, filed on Feb. 2, 2012, and Korean Patent Application No. 10-2011-0007464, filed on Jan. 25, 2011, the entire disclosures of which are incorporated herein by reference for all purposes.

TECHNICAL FIELD

Embodiments relate to an injection simulation system and an injection simulation method.

BACKGROUND ART

Medical simulation provides easier and realistic learning and training in medical fields and allows medical professionals to experience various medical situations. In particular, training on injection such as intravenous injection is fundamental in medical training since it is widely used and requires repeated learning. Medical simulation of injection allows repeated learning and training without risk to patients.

The existing injection simulation systems include one using a haptic interface to provide a tactile sensation similar to that of the human body and one using a realistic model mimicking the human body.

In the simulation using a haptic interface, an injection needle pushes a plate while it is inserted therein. This method has the problem that an intermediate medium such as gear or belt between a motor and the plate causes loss or distortion of the force of the motor being transmitted. And, since a syringe with a different shape from that of the actual syringe is used to push the plate, there occurs an unnecessary sensation of the injection needle being pulled while the injection needle is inserted. In addition, this method cannot provide a haptic sensation when pulling off the needle.

The simulation using a realistic model requires frequent replacement of the model, which incurs inconvenience and cost. Further, a quantitative evaluation is difficult since data cannot be acquired.

DISCLOSURE

Technical Problem

The present disclosure is directed to providing an injection simulation system and an injection simulation method enabling effective learning, training and evaluation of injection by providing realistic haptic sensation using an actual syringe.

Technical Solution

In one general aspect, the present disclosure provides an injection simulation system providing a haptic interface, including: a syringe having an injection needle; a haptic unit measuring the insertion angle and the insertion depth of the injection needle and including a motor unit driven by a haptic force corresponding to the measured insertion angle and insertion depth; and a control unit calculating the haptic force corresponding to the measured insertion angle and insertion depth and transmitting the calculated haptic force to the motor unit of the haptic unit.

According to an embodiment of the present disclosure, the injection simulation system may further include a processing unit including information about injection method and displaying evaluation information about injection result calculated using the insertion angle and the insertion depth of the injection needle and the haptic force.

According to an embodiment of the present disclosure, in another general aspect, the present disclosure provides an injection simulation method providing a haptic interface and a haptic unit providing a haptic force, including: measuring the insertion angle and the insertion depth of an injection needle inserted into an injection hole of the haptic unit; calculating a haptic force corresponding to the measured insertion angle and insertion depth; and driving a motor using the calculated haptic force.

According to other embodiment of the present disclosure, the injection simulation method may further include: measuring the insertion angle and the insertion depth of the injection needle; and displaying evaluation information about injection result calculated from the calculating the haptic force.

According to another embodiment of the present disclosure, the injection simulation method may further include: sensing the measurement value of the sensor mounted at the sensor; and providing an injection action as an image using the measurement value of the sensor and the insertion angle and the insertion depth of the injection needle.

Advantageous Effects

Since the injection simulation system and the injection simulation method according to the present disclosure enable realistic experience of the whole procedure of injection using a haptic interface and an actual syringe as well as quantitative evaluation of the injection result, they can be usefully used for medical education and injection training.

DESCRIPTION OF DRAWINGS

FIG. 6 is a schematic flowchart of an injection simulation method according to an embodiment of the present disclosure.

MODE FOR INVENTION

Hereinafter, the specific embodiments of the present disclosure will be described in detail with reference to accompanying drawings.

Figure 1:
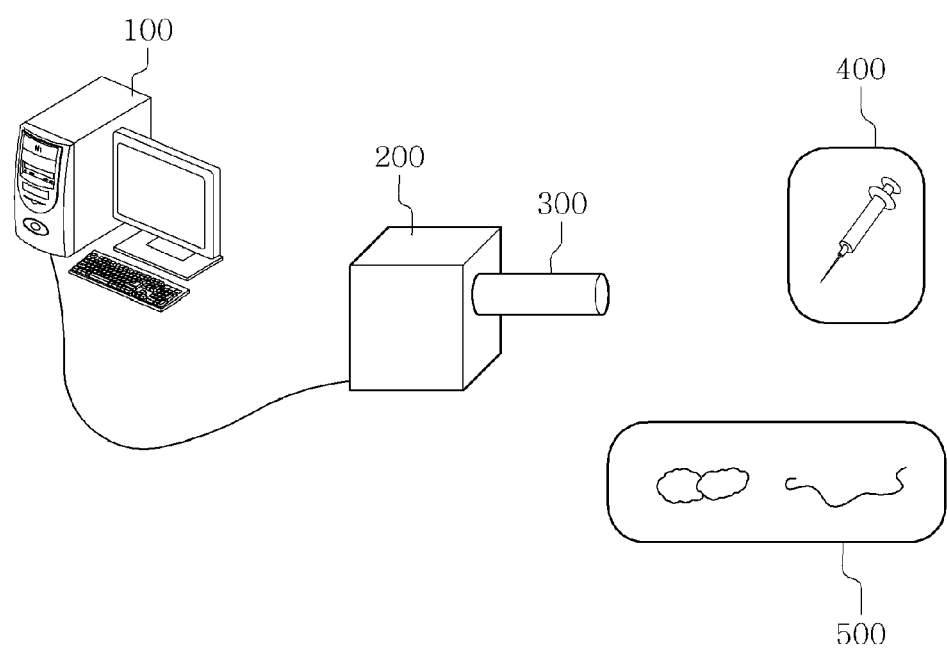
FIG. 1 is a schematic view of an injection simulation system according to an embodiment of the present disclosure.

FIG. 1 is a schematic view of an injection simulation system according to an embodiment of the present disclosure.

Referring to FIG. 1, an injection simulation system according to an embodiment of the present disclosure comprises a syringe 400, a haptic unit 300, a control unit 200 and a processing unit 100. In another embodiment, it may further comprise an auxiliary apparatus 500.

Figure 7A:
FIG. 7a is a schematic view of an injection needle used in an injection simulation system according to an embodiment of the present disclosure.
Figure 7B:
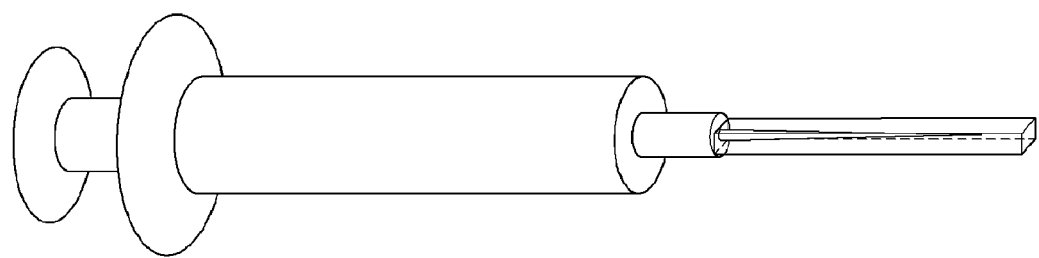
FIG. 7b is a schematic view of a syringe coupled with an injection needle used in an injection simulation system according to an embodiment of the present disclosure.

The syringe 400 comprises an injection needle inserted into an injection hole 305 of the haptic unit 300 and may be configured to have a shape the same as that of the commonly used syringe. Also, a pressure sensor, a magnetic sensor, a micro switch, an acceleration sensor, an LED, a buzzer, etc. may be built in the syringe 400 in order to determine whether it is used at proper time and position. Also, the injection needle of the syringe 400 may be coated with SF or rubber in order to increase friction. Alternatively, a wide plate made of a transparent material and an actual catheter may be coupled to increase friction, in this case, an actual syringe may be used to perform, for example, intravenous injection. FIG. 7a shows an exemplary injection needle where a plate made of a transparent material and an actual catheter are coupled, and FIG. 7b shows an example wherein the injection needle is coupled with a syringe. The end portion of the plate may be rounded so that it can be softly inserted into the injection hole 305. However, the foregoing description is only exemplary and any frictional member may be coupled with the injection needle to provide friction.

The haptic unit 300 provides a haptic effect to increase realistic sensation. The haptic unit 300 will be described in detail referring to FIG. 2 and FIG. 3.

Figure 2:
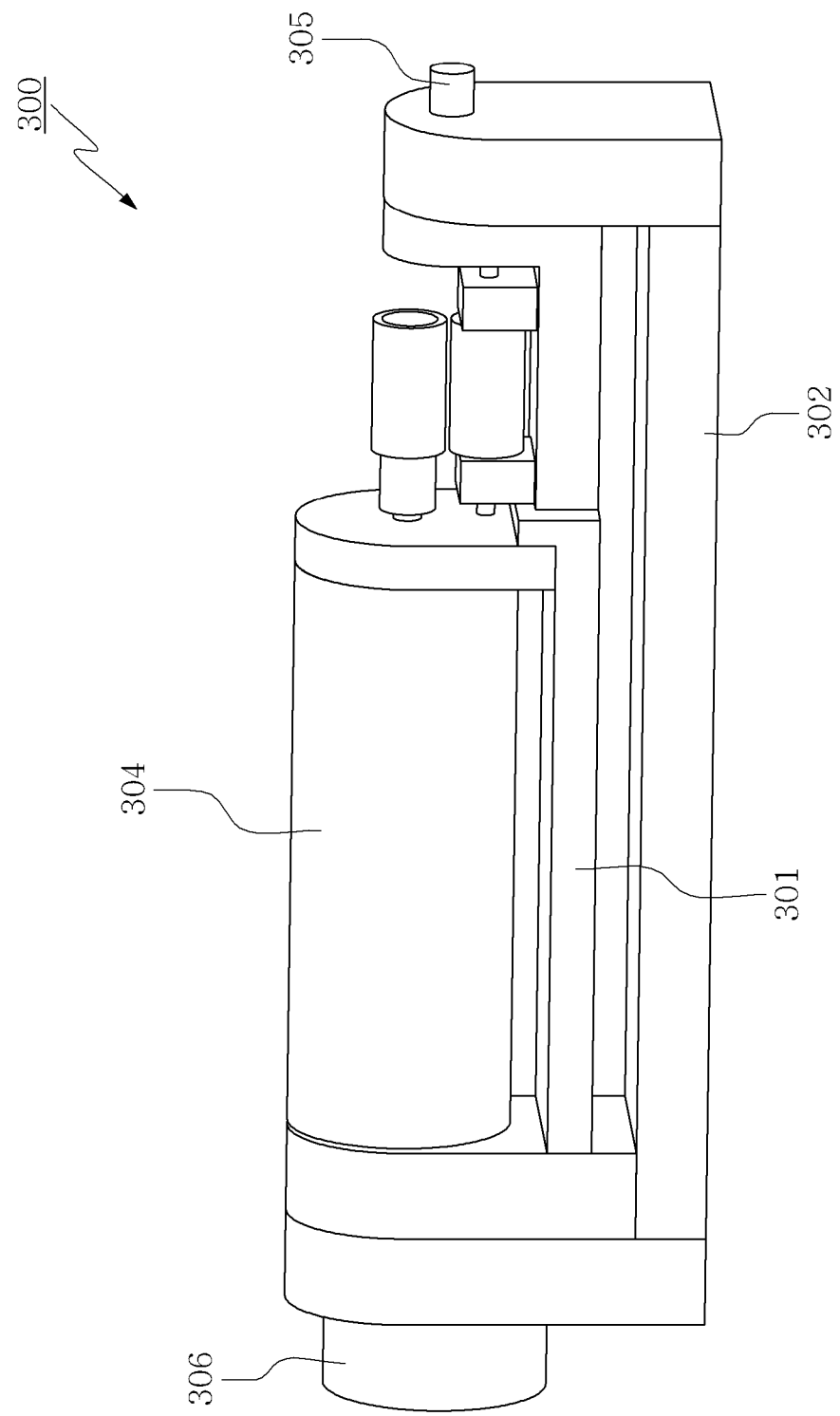
FIG. 2 is a perspective view of a haptic unit of an injection simulation system according to an embodiment of the present disclosure.
Figure 3A:
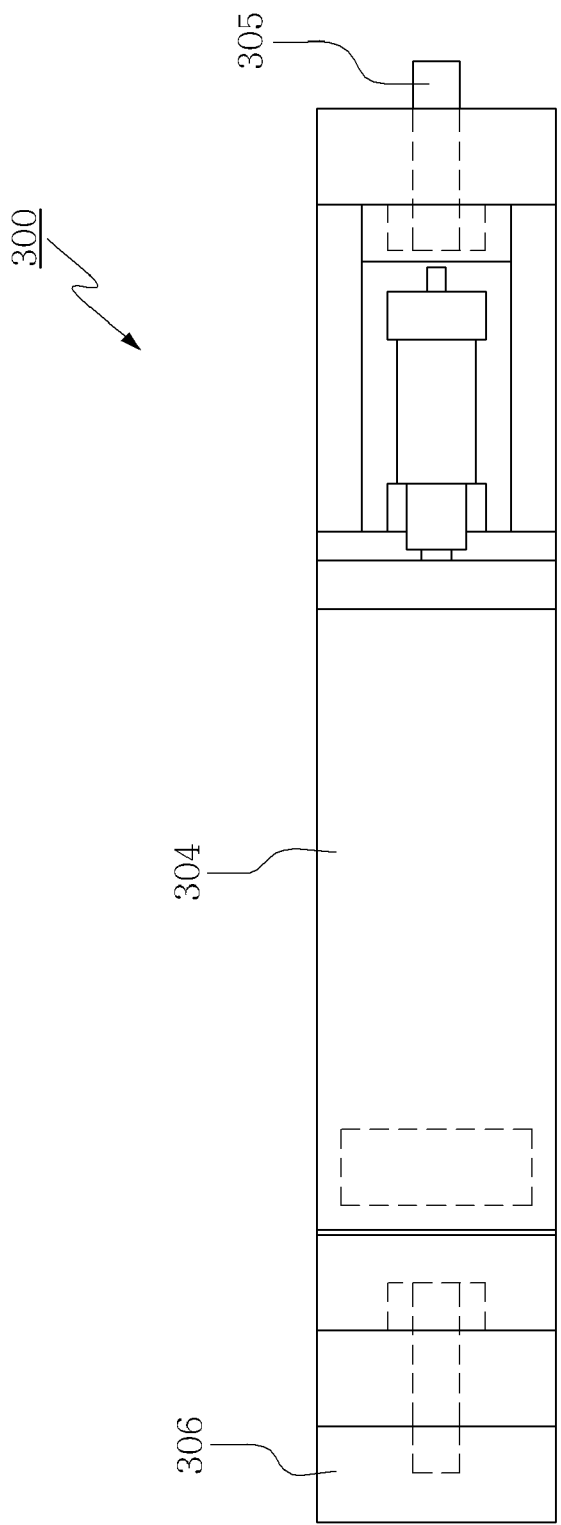
FIG. 3a is a plan view of a haptic unit of an injection simulation system according to an embodiment of the present disclosure.
Figure 3B:
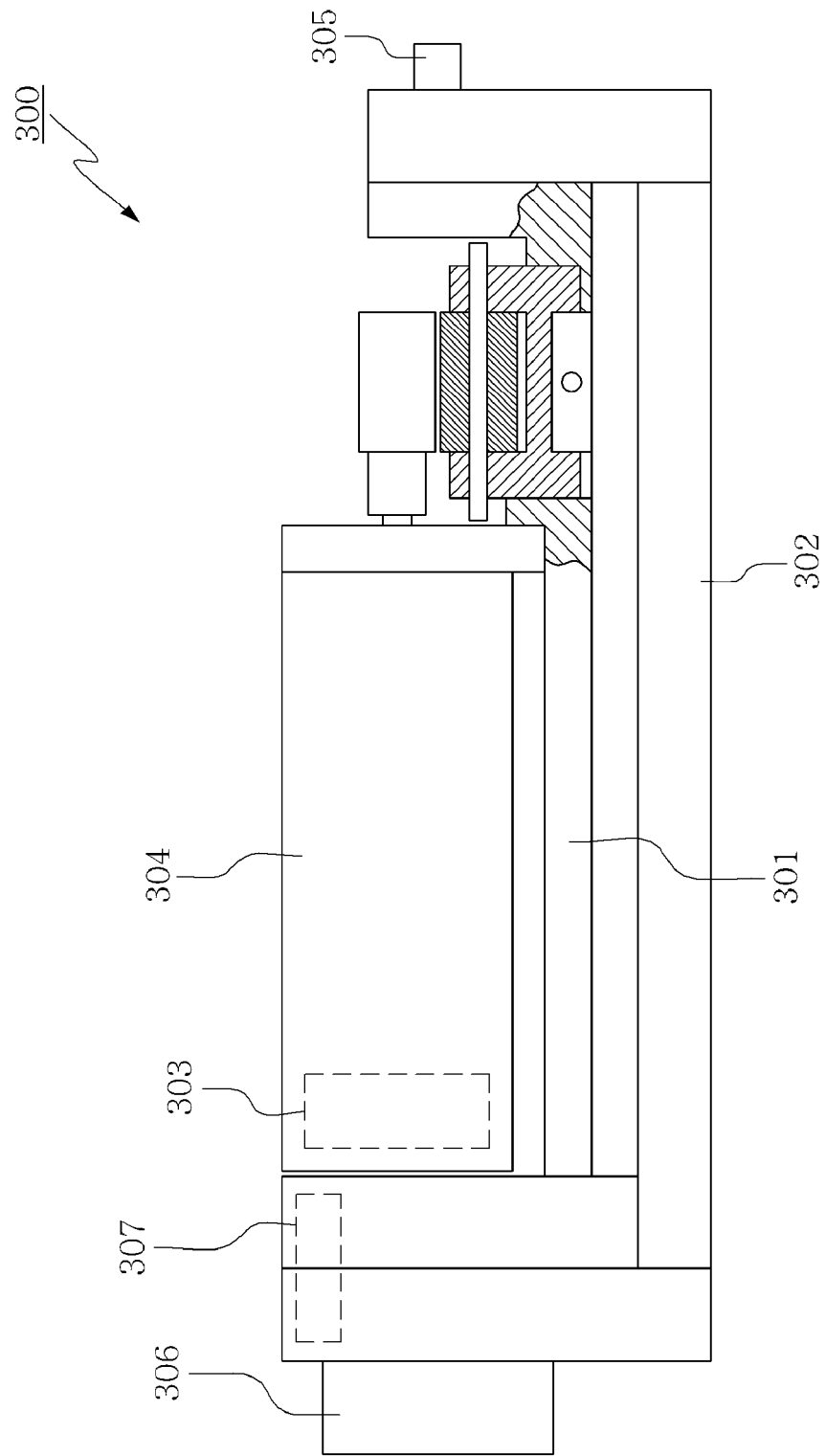
FIG. 3b is a side view of a haptic unit of an injection simulation system according to an embodiment of the present disclosure.

FIG. 2 is a perspective view of an exemplary haptic unit of an injection simulation system according to an embodiment of the present disclosure, and FIG. 3a and FIG. 3b are plan view and side view of the haptic unit, respectively.

Referring to FIG. 2, FIG. 3a and FIG. 3b, the haptic unit 300 may comprise an internal structure 301 for providing a haptic effect as if the injection needle passes through the skin, muscle, blood vessel, etc. when it is inserted and an external structure 302 for measuring the insertion angle of the injection needle. The haptic unit 300 may be configured such that the internal structure 301 is rotatable inside the external structure 302 and the tilt angle of the internal structure 301 varies according to the insertion angle of the injection needle. The insertion angle of the injection needle can be measured using the tilt angle.

The internal structure 301 may comprise a first encoder 303 sensing the insertion depth of the injection needle, a motor unit 304 being driven by a haptic force corresponding to the insertion depth and an injection hole 305 into which the injection needle is inserted. That is to say, when the injection needle is inserted into the injection hole 305, the first encoder 303 measures the insertion depth and the motor unit 304 is driven by a haptic force corresponding to the insertion depth as if the injection needle passes through the skin, muscle, blood vessel, etc. The injection hole 305 may be designed to increase friction with the injection needle, which will be described in detail later.

The external structure 302 may comprise a second encoder 306 or a tilt sensor (not shown) for measuring the tilt angle of the internal structure 301 and a fixing support 307 for setting the initial insertion angle of the injection needle. As described above, the haptic unit 300 is configured such that the internal structure 301 is rotatable inside the external structure 302 and the insertion angle of the injection needle can be measured according thereto. That is to say, when the injection needle is inserted and the insertion angle is varied by tilting the injection needle, the internal structure 301 is also tilted together with the injection needle and the second encoder 306 or the tilt sensor (not shown) attached to the external structure 302 can measure the insertion angle of the injection needle by measuring the tilting, i.e. the degree of rotation, of the internal structure 301.

The fixing support 307 is needed to set the initial insertion angle of the injection needle. The injection simulation system according to the present disclosure may adjust the initial insertion angle of the injection hole 305 using the weight of the internal structure 301 and the fixing support 307 in order to reduce cost and avoid complexity in design. To take intravenous injection for example, the insertion angle is about 15° and the injection simulation system according to the present disclosure may fix the fixing support 307 at a position where the injection hole 305 is at about 15° for simulation of intravenous injection. In this case, the injection needle is inserted smoothly when it is inserted at about 15° and, even when the needle is moved after the injection, it returns to the initial position of about 15° after the needle is pulled out due to the own weight of the internal structure 301. For simulation of injection other than the intravenous injection, the fixing support 307 may be adjusted to an insertion angle appropriate to the corresponding injection in a similar manner.

Figure 4:
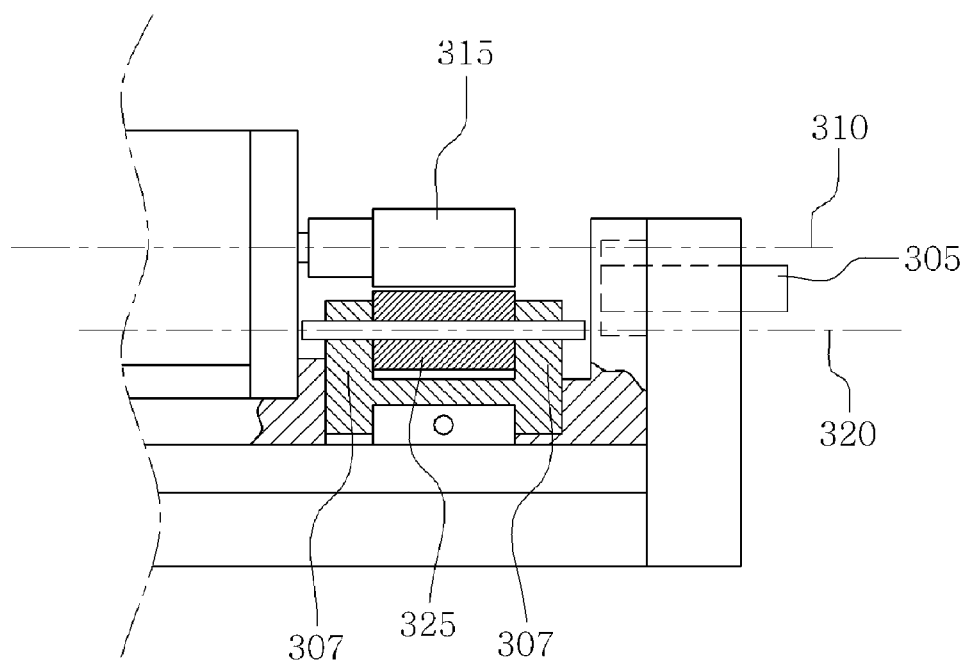
FIG. 4 is an enlarged view of an injection hole of a haptic unit of an injection simulation system according to an embodiment of the present disclosure.

FIG. 4 is an enlarged view of an injection hole of a haptic unit of an injection simulation system according to an embodiment of the present disclosure.

Referring to FIG. 4, the injection hole 305 is connected by passing through the external structure 302 and the internal structure 301, and the injection hole 305 comprises a first rotating unit 315 directly connected to a shaft of a motor unit 304 and transmitting a haptic force inside the internal structure 301 and a second rotating unit 325 the height of which is controllable. The first rotating unit 315 rotates about a first axis of rotation 310 such as the motor unit 304, and the second rotating unit 325 rotates about a second axis of rotation 320. According to the present disclosure, a high-quality haptic sensation can be provided without loss or distortion of the force of the motor being transmitted via an intermediate medium such as gear or belt unlike the existing technique, since the first axis of rotation 310 of the motor unit 304 is directly connected to the first rotating unit 315 for transmission of the force. As a result, the haptic sensation may be provided not only when the injection needle is inserted but also when it is pulled out. The first rotating unit 315 and the second rotating unit 325 provide the haptic sensation without loss or distortion using friction with the injection needle, which is not greater than the maximum static friction.

Alternatively, the first rotating unit 315 and the second rotating unit 325 may be coated with urethane to increase friction with the injection needle, and the control unit 200 may control the friction of the injection needle with the first rotating unit 315 and the second rotating unit 325 by adjusting the location of the second axis of rotation 320 upward or downward using a fixing support 307 and thereby adjusting the gap between the first rotating unit 315 and the second rotating unit 325. Of course, it may be configured such that the height of the first axis of rotation 310 is adjusted together or only the height of the first axis of rotation 310 is adjustable.

Referring back to FIG. 1, the control unit 200 calculates the haptic force for driving the motor unit 304 corresponding to the insertion depth of the injection needle measured by the haptic unit 300 and drives the motor unit 304 of the haptic unit 300 based on the calculation result. To detailed description of the control unit 200, FIG. 4 is referred.

Figure 5:
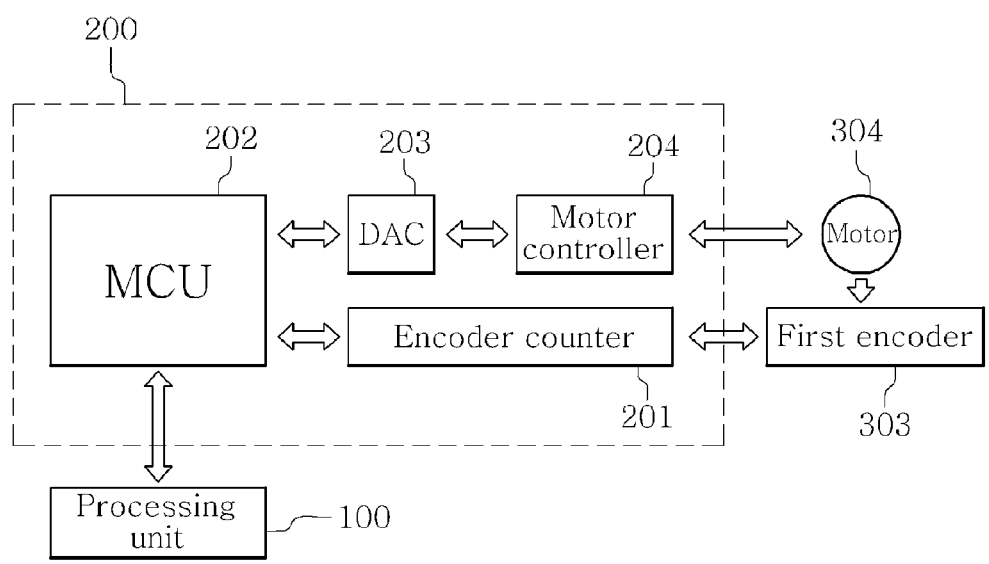
FIG. 5 is a schematic block diagram of a control unit of an injection simulation system according to an embodiment of the present disclosure.

FIG. 5 is a schematic block diagram of a control unit of an injection simulation system according to an embodiment of the present disclosure. FIG. 5 shows an exemplary block diagram of a control unit that can be used in the injection simulation system according to the present disclosure and the scope of the present disclosure is not limited thereto. Accordingly, all the elements of the control unit shown in FIG. 5 are not essential elements but addition, deletion or modification may be made if necessary.

Referring to FIG. 5, an injection needle of a syringe 400 is inserted into an injection hole 305 of a haptic unit 300, and a first encoder 303 of the haptic unit 300 measures the insertion depth of the injection needle. The first encoder 303 transmits the measured insertion depth to an encoder counter 201, and the encoder counter 201 counts the measured insertion depth and transmits the result to an MCU 202. Then, the MCU 202 calculates a haptic force for driving a motor 304. The calculation result from the MCU 202 is converted into an analog value by a digital-to-analog converter (DAC) 203, and a motor controller 204 drives the motor 304 with a torque corresponding to the converted analog value. The torque calculated by the MCU 202 can be altered to be programmable and, as a result, the injection simulation system according to the present disclosure can be applied to various parts of injection including the back of the hand, collarbone and buttock and various injection methods including intravenous, intramuscular and subcutaneous injection. The control unit 200 may communicate with a processing unit 100 via, for example, RS-232 to receive and send information.

Referring again to FIG. 1, the processing unit 100 processes information input from the syringe 400 and the haptic unit 300 so that a user can learn and practice injection and quantitatively evaluate the result. The processing unit 100 comprises information about injection method so that the user can learn how to inject and allows the user to train injection while viewing a virtual image or an image synchronized with the actual image. That is to say, the processing unit 100 may provide the injection action as an image using the measurement value from the sensors mounted to the syringe 400 and the measured insertion angle and insertion depth of the injection needle. Also, the processing unit 100 evaluates the calculated injection result using the insertion angle and insertion depth of the injection needle measured by the haptic unit 300 and the haptic force calculated by the control unit 200.

In other words, the processing unit 100 provides the user the information about injection method before practicing injection so that the user can learn how to inject, senses the injection procedure using the sensor of the syringe 400, the encoder of the haptic unit 300, or the like, allows injection training by providing a virtual image or an image synchronized with the actual image, and evaluates the result. The evaluation result may be provided as scores for quantitative evaluation.

The processing unit 100 comprises a display for displaying the information about injection method, the virtual or actual image and the injection result. Using the image displayed by the display, the user can change the part of injection such as the back of the hand, collarbone and buttock or the injection method such as intravenous, intramuscular and subcutaneous injection.

The processing unit 100 may be configured as an application software for performing the aforesaid actions and a computer system for running the software. Although the processing unit 100 is shown as a computer system in FIG. 1, it is only exemplary, and the processing unit 100 may also be configured as other systems such as a mobile terminal, a mobile phone, etc. as occasion demands.

Referring to FIG. 1, the auxiliary apparatus 500 may be used as an auxiliary means during injection. The auxiliary apparatus 500 is not an essential means but may be added or deleted as occasion demands. The auxiliary apparatus 500 may comprise artificial skin, tourniquet, alcohol swab, cannula, or the like. The auxiliary apparatus 500 may have the same as that of commonly used ones, like the syringe 400, and a pressure sensor, a magnetic sensor, a micro switch, an acceleration sensor, an LED, a buzzer, etc. may be built in the auxiliary apparatus 500 in order to determine whether it is used at proper time and position.

If the auxiliary apparatus 500 is used in the injection simulation system according to the present disclosure, the processing unit 100 may evaluate the calculated injection result using not only the insertion angle and insertion depth of the injection needle and the haptic force but also the time and position of the auxiliary apparatus 500.

FIG. 6 is a schematic flowchart of an injection simulation method according to an embodiment of the present disclosure.

Referring to FIG. 6, when a user inserts an injection needle into an injection hole 305 of a haptic unit 300 (S601), the haptic unit 300 measures the insertion angle and the insertion depth of the injection needle (S602). A control unit 200 receives the measured insertion angle and insertion depth of the injection needle and calculates a haptic force corresponding thereto (S603). Then, the haptic unit 300 drives a motor unit 304 using the calculated haptic force (S604). Through this procedure, the user can feel a realistic sensation as if he/she actually gives injection to a patient.

Subsequently, the injection result is evaluated from the result of S602 and S603 and the evaluation information is displayed (S605). Through S605, the user can quantitatively evaluate the injection result.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. An injection simulation system providing a haptic interface, comprising:
   a syringe comprising an injection needle;
   a haptic unit comprising an internal structure configured to rotate corresponding to the insertion angle of the injection needle and comprising a motor unit, the haptic unit configured to measure the insertion angle and the insertion depth of the injection needle using the rotation of the internal structure, and the motor unit configured to be driven by a haptic force corresponding to the measured insertion angle and insertion depth; and
   a control unit configured to calculate the haptic force corresponding to the insertion angle and the insertion depth and to transmit the calculated haptic force to the motor unit of the haptic unit,
   wherein the injection hole comprises
      a first rotating unit directly connected to a shaft of the motor unit and configured to transmit the haptic force; and
      a second rotating unit the height of which is controllable, wherein the injection needle is inserted between the first rotating unit and the second rotating unit;
   the injection needle comprises flat-shaped thin panel which increase an area of contact with the first rotating unit and the second rotating unit; and the first rotating unit and the second rotating unit are coated with urethane to increase friction with the injection needle.

2. The injection simulation system according to claim 1, which further comprises a processing unit comprising information about injection method and configured to display evaluation information about injection result calculated using the insertion angle and the insertion depth of the injection needle and the haptic force.

3. The injection simulation system according to claim 1, wherein at least one of a pressure sensor, a magnetic sensor, a micro switch, an acceleration sensor, a display and a buzzer is mounted to the syringe.

4. The injection simulation system according to claim 1, wherein the internal structure further comprises:
    a first encoder configured to sense the insertion depth of the injection needle; and
    an injection hole into which the injection needle is inserted.

5. The injection simulation system according to claim 1, wherein the injection needle is coupled with a friction unit for generating friction with the first rotating unit and the second rotating unit.

6. The injection simulation system according to claim 5, wherein the control unit is configured to control the friction of the injection needle with the first rotating unit and the second rotating unit by adjusting the height of the second rotating unit.

7. The injection simulation system according to claim 1, wherein the haptic unit further comprises an external structure comprising:
    a second encoder or a tilt sensor configured to measure the insertion angle of the injection needle using the rotation of the internal structure; and
    a fixing support configured to set the initial insertion angle of the injection needle.

8. The injection simulation system according to claim 1, which further comprises an auxiliary apparatus comprising at least one of artificial skin, tourniquet, alcohol swab and cannula.

9. The injection simulation system according to claim 8, which further comprises a processing unit comprising information about injection method and configured to display evaluation information about injection result calculated using the insertion angle and the insertion depth of the injection needle, the time and position of the auxiliary apparatus and the haptic force.

10. The injection simulation system according to claim 8, wherein at least one selected from a pressure sensor, a magnetic sensor, a micro switch, an acceleration sensor, a display and a buzzer is mounted to the auxiliary apparatus.

11. An injection simulation method providing a haptic interface using a haptic unit providing the haptic force and a syringe, comprising:
    measuring the insertion angle and the insertion depth of an injection needle of the syringe inserted into an injection hole of the haptic unit using the rotation of an internal structure of the haptic unit rotating corresponding to the insertion angle of the injection needle;
    calculating the haptic force corresponding to the measured insertion angle and insertion depth; and
    driving a motor of the haptic unit using the calculated haptic force,
    wherein the injection hole comprises
        a first rotating unit directly connected to a shaft of the motor unit and transmitting the haptic force; and
        a second rotating unit having a height thereof which is controllable,
    wherein the injection needle is inserted between the first rotating unit and the second rotating unit;
    the injection needle comprises flat-shaped thin panel which increase an area of contact with the first rotating unit and the second rotating unit; and
    the first rotating unit and the second rotating unit are coated with urethane to increase friction with the injection needle.

12. The injection simulation method according to claim 11, which further comprises:
    measuring the insertion angle and the insertion depth of the injection needle; and
    displaying evaluation information about injection result calculated from said calculating the haptic force.

13. The injection simulation method according to claim 11, which further comprises:
    mounting at least one of a pressure sensor, a magnetic sensor, a micro switch, an acceleration sensor, a display and a buzzer to the syringe, and sensing the measurement value of the sensor; and
    providing an injection action as an image using the measurement value of the sensor and the insertion angle and the insertion depth of the injection needle.

* * * * *